United States Patent [19]

Edwards

[11] 4,360,025
[45] Nov. 23, 1982

[54] CATHETER RETAINER

[75] Inventor: John V. Edwards, East Grinstead, England

[73] Assignee: Kingsdown Medical Consultants, Ltd., England

[21] Appl. No.: 242,776

[22] Filed: Mar. 11, 1981

[30] Foreign Application Priority Data

Apr. 1, 1980 [GB] United Kingdom ............... 8010860

[51] Int. Cl.³ .......................................... A61M 25/00
[52] U.S. Cl. ........................... 604/180; 128/DIG. 26; 604/336; 604/338
[58] Field of Search ............................ 128/348–351, 128/276, 283, DIG. 26

[56] References Cited

U.S. PATENT DOCUMENTS 3,339,546  9/1967  Chen ................................ 128/156
3,602,227  8/1971  Andrew ........................... 128/351
4,170,995  10/1979 Levine et al. ................. 128/DIG. 26
4,249,529  2/1981  Nestor et al. ................ 128/DIG. 26

FOREIGN PATENT DOCUMENTS 865521   10/1978  Belgium .
932366   7/1963   United Kingdom .
1234375  6/1971   United Kingdom .
1355888  6/1974   United Kingdom .
1457004  12/1976  United Kingdom .
1505349  3/1978   United Kingdom .
1507329  4/1978   United Kingdom .
1571657  7/1980   United Kingdom .

Primary Examiner—Richard J. Apley
Assistant Examiner—T. J. Wallen
Attorney, Agent, or Firm—Lawrence S. Levinson; Stephen B. Davis

[57] ABSTRACT

A catheter retainer comprising a member of synthetic plastics material having a central hole wholly or partly defined by a pair of resilient catheter-gripping jaws, and a resilient catch member for holding the jaws in their relatively closed position. The catheter retainer is preferably an insert that snaps into a coupling member which is carried by a pad of adhesive dressing material.

8 Claims, 2 Drawing Figures

CATHETER RETAINER

BACKGROUND OF THE INVENTION

Catheters and tubing of various type and size often have to be retained in a patient for extended periods of time. This invention is directed to a catheter retainer which can accommodate different size catheters and tubes and securely hold them in position. The catheter retainer of this invention is easy to manipulate.

Steer et al. in British Pat. No. 1,571,657 disclose a two piece coupling system designed to retain an ostomy pouch around a stomal opening.

Chen in U.S. Pat. No. 3,339,546 disclose medical grade adhesives having one or more water soluble or water swellable hydrocolloids dispersed in a viscous elastic binder.

SUMMARY OF THE INVENTION

This invention is directed to a catheter retainer comprising a member of synthetic plastics material having a central hole wholly or partly defined by a pair of resilient catheter-gripping jaws, and a resilient catch member for holding the jaws in their relatively closed position. The jaws and the catch are preferably integral with and form parts of the member.

According to the preferred embodiment of the invention, there is provided a catheter retainer which comprises a pad of surgical dressing material having one surface for contacting the skin of a wearer, a central hole, and a pair of catheter gripping jaws mounted within a coupling member secured to the other surface of the pad. The jaws may be formed by two appropriately-shaped surfaces of a single insert of a resilient plastics material. The insert may be snapped into position behind a resilient flange located on the coupling. It may carry pegs by which the jaws may be opened and closed using the fingers, to release or secure the catheter as the case may be.

DETAILED DESCRIPTION OF THE INVENTION

Figure 1:
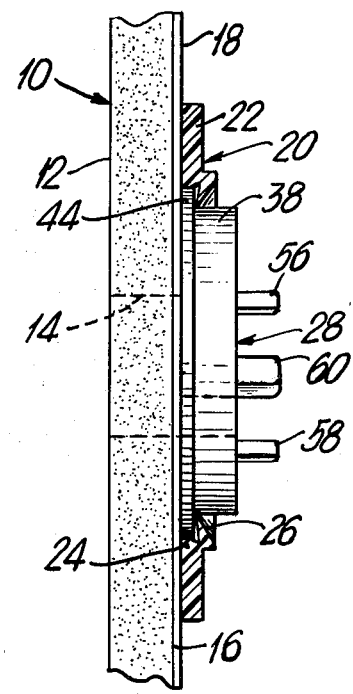
FIG. 1 is a side elevation view of one example of catheter retainer according to the invention.
Figure 2:
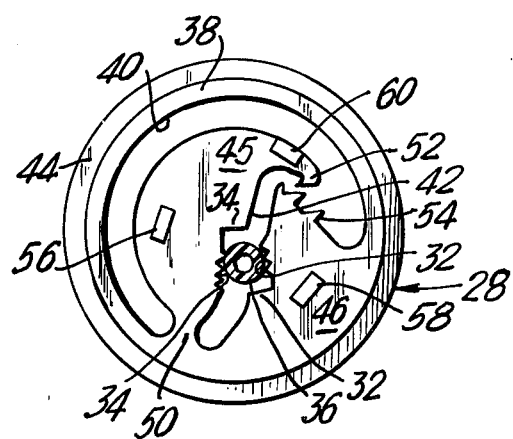
FIG. 2 is a front view of the catheter retainer illustrated in FIG. 1.

The catheter retainer illustrated in FIGS. 1 and 2 includes an adhesive pad or dressing 10 having a surface 12 for engaging the skin of the patient surrounding the region where the catheter is to be inserted. The adhesive pad or dressing 10 is of medical grade and preferably consists of one or more water soluble or swellable hydrocolloids dispersed in a viscous elastic binder as taught by Chen in U.S. Pat. No. 3,339,546. The pad 10 has an opposed surface 16 to which a layer of polymeric material 18 such as polyethylene, polyvinyl chloride, etc., is suitably bonded. A hole 14 is provided in the pad or cut in the pad according to the size needed.

An adhesive pad having a polymeric film bonded to one side suitable for use as part of the catheter retainer of this invention is commercially available under the trademark Stomahesive.

As illustrated in the figures, a coupling member 20, preferably of circular form, is secured to layer 18. The coupling member can be affixed to layer 18 by use of adhesives, heat welding, or other suitable means. The coupling member 20 includes a flange 22, a rim 24, and resilient flexible inwardly directed skirt or strip 26 which extends around the rim. The coupling member 20 may be injection molded from any suitable synthetic plastics material. Such coupling member is taught by Steer et al. in British Pat. No. 1,571,657.

A catheter gripping disc 28 is illustrated in the figures. The disc 28 includes a marginal rim portion 44 of a diameter and axial thickness chosen to fit snugly with rim 24 and be trapped between the layer 18 and the skirt 26. The disc 28 is held in place by the resilience of the skirt 26.

This disc 28 is preferably molded from a single piece of plastics material, for example high-density polyvinyl chloride or polypropylene, and is made in a special shape to define jaws 32, 34 between which a catheter 36 or other tube can be clamped. As seen in FIG. 2, the disc 28 has a central portion 38 that includes an arcuate hole 40 that mergers with a catheter slot 42, a first limb section 45, and a base pad 46. The limb 45 is connected to pad 46 by an integral hinge 50, the limb 45 thereby being enabled to oscillate about the hinge 50 in the plane of the disc. The other end of the limb has a hook 52 which co-operates with a series of hooks or notches 54 on the base pad 46. Jaws 34 on the limb 45 are disposed opposite to jaws 32 on the base pad 46 and a catheter 36, in use, is gripped between the jaws when the hook 52 is engaged with an appropriate one of the notches 54. Although only two notches 54 are illustrated, obviously more notches may be provided. In this way a number of different catheters of different external diameters may be held in position.

This disc 28 has three upstanding pegs 56, 58 and 60 to allow manipulation of the limb 45 relative to the base pad 46. The pegs 56 and 58 are squeezed towards each other using for example the thumb and first finger in order to grip a catheter between the jaws; in this operation the resilience of the hook 52 causes it to tend to engage one of the notches or hooks 54. In order to release the catheter, the peg 60 is lifted (i.e. pulled away from the peg 58) so disengaging the hook 54 from its associated notch and allowing the limb 45 to spring back in a generally anticlockwise direction as seen in FIG. 2.

The configuration of marginal rim 44 is chosen in accordance with the configuration of coupling member 20. Thus, it is preferred that both be circular. Similarly, the configuration of central portion 38 can be varied but it is preferred that it be circular and extend upwards from rim 44.

The disc 28 can be sold separately from the pad-coupling 20 combination, and can readily be snapped into the coupling thereof when it is desired to convert a pad-coupling combination from ostomy bag use to catheter retaining use.

In an alternative embodiment of the invention, the disc embodying catheter-gripping jaws may be carried by any suitable support and may be secured to the body of the user in any convenient way, e.g., by adhesive.

Accordingly the present invention resides in a disc of resilient plastics material comprising a pair of jaws capable of gripping a catheter and holdable together by a catch and notch arrangement, or its mechanical equivalent.

It will be appreciated that variations may be made in the particular shapes and materials herein disclosed, without departing from the invention. In this specification the term "catheter retainer" is intended to include a retainer for retaining in position tubing which extends into a human or an animal body.

What is claimed is:

1. A catheter retainer comprising a pad of adhesive dressing material having one surface for contacting the skin of a wearer and a central opening, a coupling member having a flange permanently affixed to the other surface of said adhesive pad around said opening, said coupling member also including an upstanding rim and an resilient flexible skirt projecting inwardly from the periphery of said rim, and a catheter retainer insert dimensioned to fit within said coupling member rim and be held in place by said resilient skirt, said catheter retainer comprising a member of synthetic plastics material having a central hole wholly or partly defined by a pair of resilient catheter-gripping jaws, and a resilient catch member for holding the jaws in their relatively closed position.

2. A catheter retainer according to claim 1 in which the insert carries pegs to enable finger manipulation of the jaws.

3. A catheter retainer according to claim 1 in which said coupling member and said catheter retainer insert are of circular configuration.

4. A catheter retainer according to claim 1 in which said adhesive pad has a film of polymeric material on the surface which does not contact the body and the flange of said coupling member is welded or adhesively affixed to said polymeric film.

5. A catheter retainer capable of holding catheters of varying external diameter in position, said retainer being formed from a single piece of plastics material and comprising a disc having a marginal rim portion and a central portion which includes an arcuate hole that merges with a catheter slot, a limb section, and a base pad, one end of said limb being connected to said base pad by an integral hinge thereby enabling said limb to oscillate about said hinge in the plane of the disc, the other end of said limb having a hook which cooperates with a series of notches on said base pad, said catheter slot positioned between opposing walls of said limb and said base pad with a series of catheter gripping jaws on these opposing limb and base pad walls.

6. The catheter retainer of claim 5 wherein said limb and said base pad have upstanding pegs which allow finger manipulation of said limb relative to said base pad.

7. A catheter retainer capable of holding catheters of varying external diameter in position, said retainer comprising an adhesive dressing one surface of which adheres the retainer to the skin, said dressing having a central opening, a coupling member having a flange permanently affixed to the other surface of said dressing around said central opening, said coupling member also having an upstanding rim and a resilient flexible skirt projecting inwardly from the periphery of said rim, and a catheter retainer insert formed from a single piece of plastics material comprising a disc having a marginal rim portion and a central portion, said marginal rim portion dimensioned to fit between said coupling member rim and said dressing and be held in place by said resilient skirt, said disc central portion including an arcuate hole that merges with a catheter slot, a limb section, and a base pad, one end of said limb being connected to said base pad by an integral hinge thereby enabling said limb to oscillate about said hinge in the plane of the disc, the other end of said limb having a hook which cooperates with a series of notches on said base pad, said catheter slot positioned between opposing walls of said limb and said base pad with a series of catheter gripping jaws on these opposing limb and base pad walls.

8. The catheter retainer of claim 7 wherein said limb and said base pad having upstanding pegs which allow finger manipulation of said limb relative to said base pad.

* * * * *